US006004304A

United States Patent [19]

Suzuki et al.

[11] Patent Number: 6,004,304

[45] Date of Patent: Dec. 21, 1999

[54] SUBCUTANEOUS NEEDLE AND METHOD OF PRODUCING THE SAME

[75] Inventors: Tsuyoshi Suzuki; Shigeaki Ide; Masatoshi Yamamoto, all of Shimizu, Japan

[73] Assignee: Seirin Kasei Co., Ltd., Japan

[21] Appl. No.: 09/177,382

[22] Filed: Oct. 23, 1998

[30] Foreign Application Priority Data

Aug. 12, 1998 [JP] Japan .................................. 10-228107

[51] Int. Cl.$^{6}$ ...................................................... A61M 5/32

[52] U.S. Cl. ............................................ 604/272; 604/180

[58] Field of Search ..................................... 604/272, 275, 604/274, 308, 309, 502, 115, 117, 175, 180, 174; 601/134; 606/204, 223

[56] References Cited

U.S. PATENT DOCUMENTS

| | | | |
|---|---|---|---|
| 3,753,432 | 8/1973 | Guerra | 604/167 X |
| 4,355,751 | 10/1982 | Kapitanov et al. | 227/19 |
| 4,861,341 | 8/1989 | Woodburn | 604/272 X |
| 5,078,689 | 1/1992 | Keller | 604/174 X |
| 5,582,580 | 12/1996 | Buckman, Jr. et al. | 601/134 X |
| 5,607,407 | 3/1997 | Tolkoff et al. | 604/523 |

FOREIGN PATENT DOCUMENTS 2507120 5/1996 Japan .

*Primary Examiner*—Wynn Wood Coggins
*Assistant Examiner*—Anh-Tuan T. Nguyen
*Attorney, Agent, or Firm*—Laubscher & Laubscher

[57] ABSTRACT

The present invention relates to a subcutaneous needle in which a needle body and an adhesive tape are reliably secured together with a resin material enabling the operation to be correctly executed, and a method of producing the same. The subcutaneous needle is constituted by an adhesive tape, a separate paper, a needle body and a resin material. The adhesive tape has a hole formed in the central portion and has an adhesive surface on one side thereof. The separate paper has a hole in the central portion and is stuck on the adhesive surface of the adhesive tape. The needle body is bent in an L-shape and its top end side protrudes penetrating through the holes of the adhesive tape and of the separate paper. The base end side of the needle body is arranged nearly in parallel with a nonadhesive surface of the adhesive tape. The resin material is injection-molded onto the nonadhesive surface of the adhesive tape so as to cover and secure the base end side of the needle body.

4 Claims, 3 Drawing Sheets

(A)

(B)

SUBCUTANEOUS NEEDLE AND METHOD OF PRODUCING THE SAME

TECHNICAL FIELD

The present invention relates to a subcutaneous needle used in the field of acupuncture and moxibustion in Oriental medicine and to a method of producing the same.

BACKGROUND ART

The subcutaneous needle of this kind has been disclosed in Japanese Registered Utility Model No. 2507120 being constituted by a needle body and two pieces of adhesive tapes. This subcutaneous needle is so constituted that the side of the base end of the needle body is formed into a spring shape, and is held being sandwiched between the two pieces of adhesive tapes having adhesive surfaces on the side of the top end of the needle body.

According to the above conventional subcutaneous needle, however, the seat portion of the needle body is formed in a spring shape, resulting in a complex machining step, which is not advantageous even from the standpoint of cost. Besides, the needle body is held at its seat portion being sandwiched by the two pieces of adhesive tapes and is secured by the adhesive force of these tapes, arousing problems in that the securing force is weak, and the seat portion is deviated between the adhesive tapes during the operation, causing pain.

In view of the above-mentioned problems inherent in the prior art, the object of the present invention is to provide a subcutaneous needle which can be produced through a simplified machining step as a result of simplifying the shape of the base end of the needle body and which is reliably secured onto the adhesive tape to alleviate pain at the time of operation as in the prior art, and a method of producing the subcutaneous needle.

DISCLOSURE OF THE INVENTION

The present invention therefore deals with a subcutaneous needle comprising:

a nearly circular adhesive tape having an adhesive surface on the one side thereof and a hole in the central portion thereof;

a separate paper stuck on the adhesive surface of said adhesive tape in a manner that it can be separated off and having a hole in the central portion thereof;

a needle body bent in an L-shape, the top end side thereof protruding through the holes of said adhesive tape and said separate paper, and the base end side thereof being arranged on the side of a nonadhesive surface of said adhesive tape nearly in parallel therewith; and a resin material formed on the nonadhesive surface of said adhesive tape to cover and secure the base end side of said needle body.

By forming the base end of the needle body in an L-shape which can be simply machined, the step of machining is simplified and the cost is decreased.

With the base end of the needle body being covered and secured by the resin material on the nonadhesive surface of the adhesive tape, furthermore, the needle body is reliably secured and is not deviated relative to the adhesive tape during the operation, alleviating the pain.

According to the present invention, furthermore, a flat portion is formed on the base end side of the needle body to prevent the needle body from a deviation due to rotation about the base end side as an axis, thereby to more reliably secure the needle body and the adhesive tape together.

Moreover, according to the present invention, the separate paper is divided into a side having the central hole and a side without the central hole. Thus, there can be left the side without the central hole of the separate paper that was divided into two. Therefore, if the operation is executed by pinching this portion, the fingers stay away from the adhesive portion of the adhesive tape, and the operation can be correctly executed.

The present invention provides a method of producing a subcutaneous needle comprising the steps of:

sticking a separate paper having a hole in the central portion thereof on an adhesive surface of a nearly circular adhesive tape having the adhesive surface on one side thereof and a hole in the central portion thereof in a manner that the separate paper can be separated off;

permitting the top end side of a needle body bent in an L-shape to pass through the holes of said adhesive tape and of said separate paper, and arranging the base end side of said needle body on the side of a nonadhesive surface of said adhesive tape nearly in parallel therewith; and injection-molding a resin material onto the nonadhesive surface of said adhesive tape so as to cover the base end side of said needle body.

According to this method, the needle body and the adhesive tape are secured together by means of injection-molding of the resin material, thus enabling the subcutaneous needles to be easily and stably produced.

The characteristic constitution and the resulting action and effect of the present invention will become more obvious from the embodiment described below.

BEST MODE FOR CARRYING OUT THE INVENTION

Described hereinbelow is an embodiment of the present invention.

First, the structure of a subcutaneous needle according to an embodiment of the present invention will be described with reference to FIG. 1.

Figure 1:
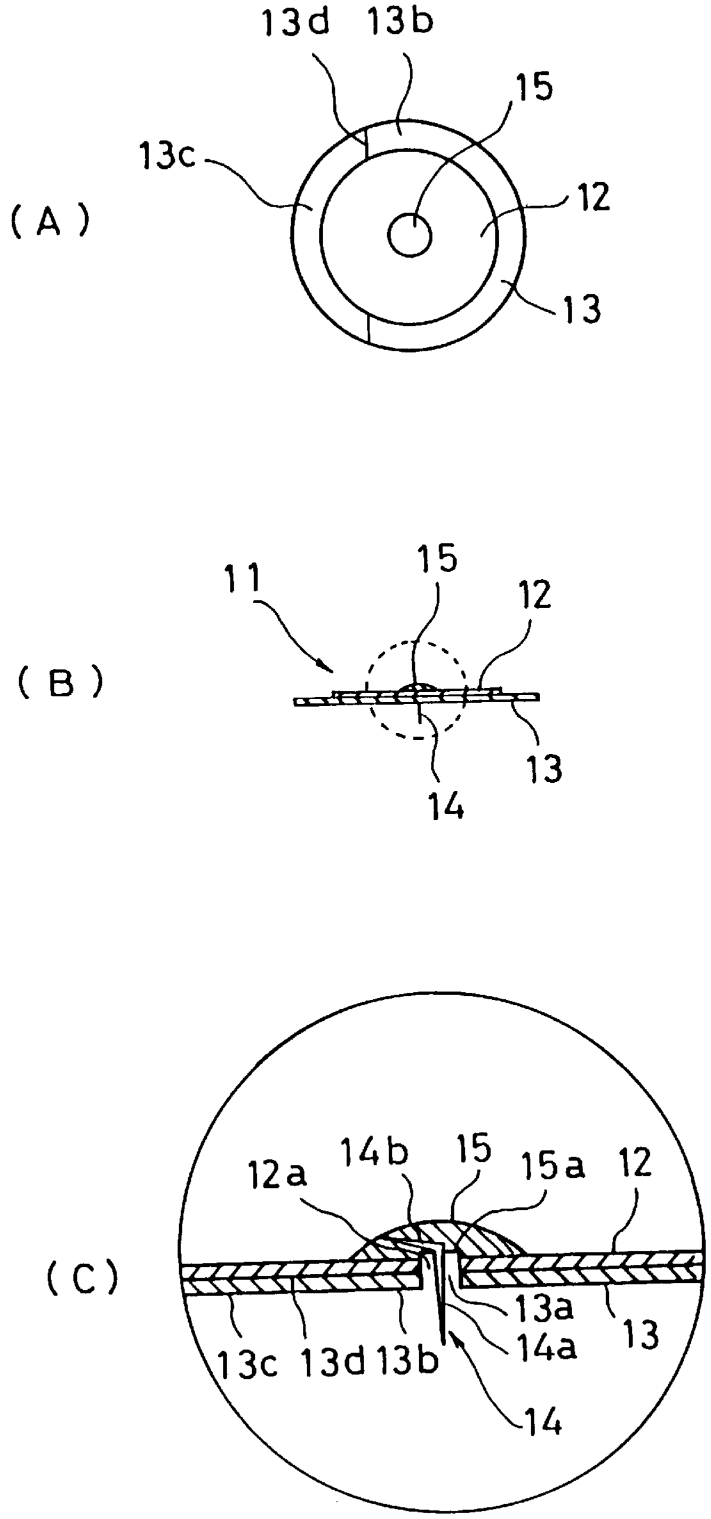
FIG. 1 is a diagram illustrating the structure of a subcutaneous needle according to an embodiment of the present invention.

In FIG. 1, FIG. 1(A) is a plan view, FIG. 1(B) is a front view, and FIG. 1(C) is an enlarged view of a region of a dotted line of FIG. 1(B).

A subcutaneous needle 11 is constituted by an adhesive tape 12, a separate paper 13, a needle body 14, and a resin material 15.

The adhesive tape 12 is made of a paper, a fabric, a nonwoven fabric or a plastic tape, has a circular shape, is adhesive on the one side thereof, and has a hole 12*a* formed in the central portion thereof.

The separate paper 13 is made of a paper, has a circular shape, has a diameter slightly larger than that of the above-mentioned adhesive tape, has a hole 13*a* formed in the central portion thereof, is divided into two at 13*d*, i.e., divided into a side 13*b* having the hole 13*a* and a side 13*c* without the hole, and is stuck on the adhesive surface of the adhesive tape 12.

By dividing the separate paper 13 into two as described above, the separate paper can be left on a portion of the adhesive surface of the adhesive tape 12, so that the needle body 14 can be easily fitted to an acupuncture point.

The needle body 14 is made of a stainless steel and is bent in an L-shape as will be described later.

A top end side 14*a* of the needle body protrudes passing through the hole 12*a* of the adhesive tape 12 and the hole 13*a* of the separate paper 13, and the thus protruded portion is inserted into the skin.

On the other hand, the base end side 14*b* is arranged nearly in parallel with the nonadhesive surface of the adhesive tape 12.

The resin material 15 is composed of an injection molding resin, a thermosetting resin, a normal temperature-curing resin, an ultraviolet ray-curing resin or an elastomer resin, and is injection-molded onto the nonadhesive surface of the adhesive tape 12 so as to cover the base end side 14*b* of the needle body as will be described later.

In order to prevent the burring of the resin material caused by the injection molding, a dent designated at 15*a* is formed in the central portion of the resin material 15.

Next, the needle body 14 will be described in detail with reference to FIG. 2.

Figure 2:
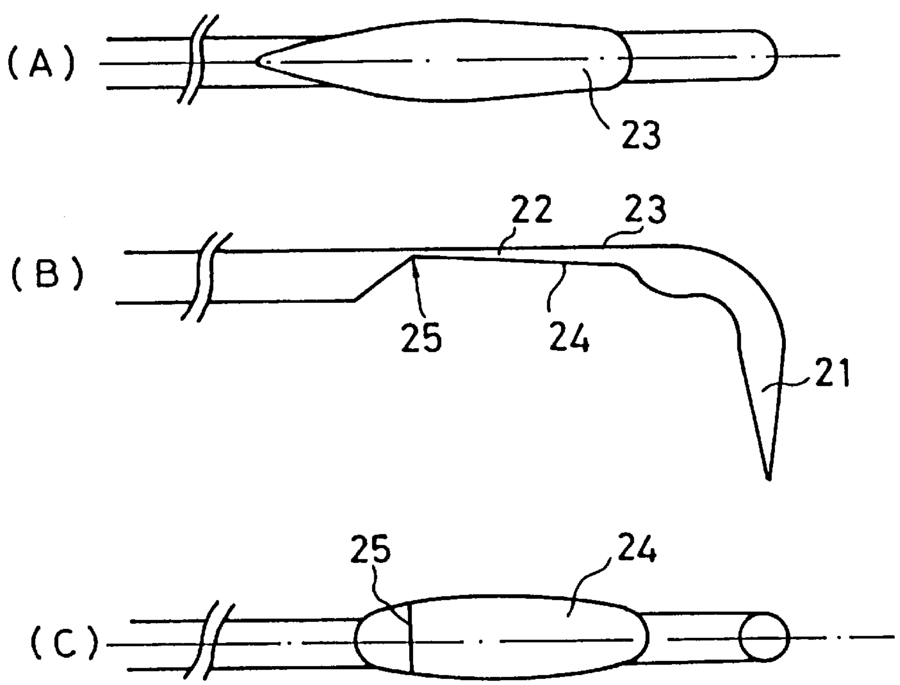
FIG. 2 is a diagram illustrating the structure of a needle body in detail.

FIG. 2 is an enlarged view of the needle body 14. For the purpose of convenience, FIG. 2 shows the needle body 14 in a state of before being cut from a base material, wherein FIG. 2(A) is a plan view, FIG. 2(B) is a front view and FIG. 2(C) is a bottom view.

First, an end of a rod-like base material is ground to form a needle portion 21 which serves as a top end of the needle body.

Then, a central side continuous to the needle portion 21 is bent, i.e., the base material is bent in an L-shape as shown. An upper surface and a lower surface of a portion 22 that is the base end side of the needle body are press-worked thereby to form an upper flat portion 23 and a lower flat portion 24. Attention must be given so that the flat portions 23 and 24 are formed without getting scarred.

Finally, a neck part 25 is cut to complete the needle body 14.

Figure 3:
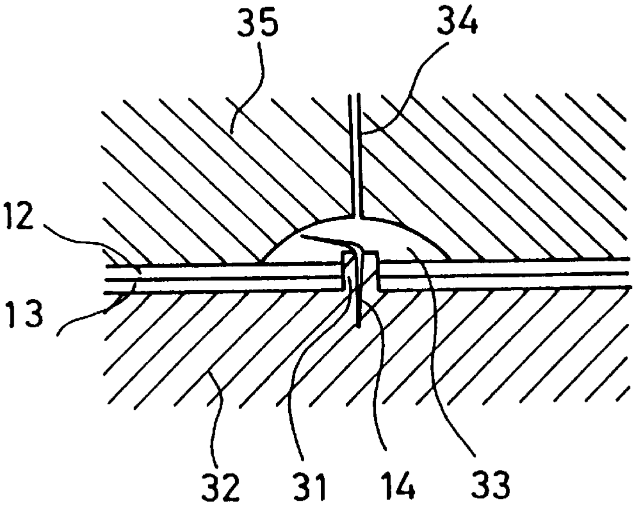
FIG. 3 is a diagram illustrating a cavity section of a mold for injection molding.

Referring next to FIG. 3, there is explained the injection-molding to secure the needle body 14 completed through the above-mentioned machining to the adhesive tape 12.

FIG. 3 shows a cavity section (hatched portion) in the mold used for the injection molding.

The cavity section is constituted by a core block 32 having an embedding base 31 for holding the needle body 14, a semispherical cavity 33, and a cavity block 35 having a runner 34.

The machining process is as described below.

First, in a state where the cavity block 35 is lifted up, the adhesive tape 12 and the separate paper 13 are placed on the core block 32 in a manner that the adhesive surface of the adhesive tape 12 faces the side of the core block 32, and the holes 12*a* and 13*a* are fitted to the embedding base 31.

Then, after the needle body 14 is placed on the embedding base 31, the cavity block 35 is lowered to be closed in a manner that the adhesive tape 12 is not broken.

In this state, the resin material is injected into the cavity 33 through the runner 34 and is cured, so that the needle body 14 is secured onto the adhesive tape 12.

Here, the height of the embedding base 31 is greater than the thickness of the adhesive tape 12 and of the separate paper 13 that are placed one upon the other. Therefore, a dent is formed as designated at 15*a* in FIG. 1, and burr is prevented from being formed.

Figure 4:
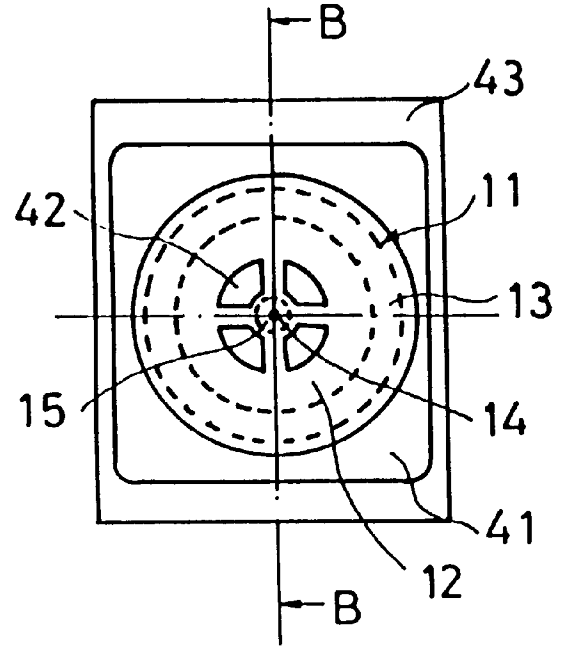
FIG. 4 is a diagram illustrating an example of a container for holding the subcutaneous needle.
Figure 4:
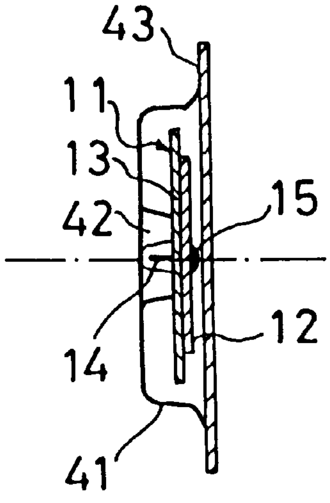

FIG. 4 illustrates an example of a container for holding the subcutaneous needle produced through the above-mentioned procedure.

To clearly show the positional relationship between the subcutaneous needle 11 and a container 41, the subcutaneous needle 11 is shown in a state of being held in the container 41.

FIG. 4(A) is a plan view and FIG. 4(B) is a side sectional view along a line B—B of FIG. 4(A).

The container 41 having a circular opening is made of a laminated film and has a diameter capable of containing the separate paper 13 of the subcutaneous needle 11. Near the central portion of the container 41, there are arranged seats 42 maintaining an equal distance in the circumferential direction to accommodate and protect the needle body 14 and to uphold the adhesive tape 12 and the separate paper 13.

The subcutaneous needle 11, after being contained in the container 41, is sealed with a sealing paper 43 and is pasteurized in a state as shown in FIG. 4.

To use the thus completed subcutaneous needle 11, after the subcutaneous needle 11 is taken out from the container 41, portions of the adhesive tape 12 and of the separate paper on the side 13*c* without hole are pinched, the side 13*b* having the hole of the separate paper is separated off, the needle body 14 is fitted to an acupuncture point and inserted therein, and an exposed portion of the adhesive surface is stuck on the skin and is secured.

Furthermore, the remaining separate paper 13*c* is separated off, and the adhesive surface of this portion is stuck on the skin, too.

According to the present invention as described above, the base end side of the needle body is formed in an L-shape which is easy to machine, resulting in decrease of the cost of working. Besides, the base end side of the needle body is reliably secured with a resin material onto the nonadhesive surface of the adhesive tape, so that the needle body is not deviated relative to the adhesive tape during the operation and that pain is minimized unlike that of the prior art. Thus, the present invention offers great industrial applicability.

What we claimed are:

1. A subcutaneous needle comprising:

a nearly circular adhesive tape having an adhesive surface on the one side thereof and a hole in the central portion thereof;

a separate paper stuck on the adhesive surface of said adhesive tape in a manner that it can be separated off and having a hole in the central portion thereof;

a needle body bent in an L-shape, the top end side thereof protruding through the holes of said adhesive tape and said separate paper, and the base end thereof being arranged on the side of a nonadhesive surface of said adhesive tape nearly in parallel therewith; and a resin material formed on the nonadhesive surface of said adhesive tape to cover and secure the base end side of said needle body.

2. A subcutaneous needle according to claim 1, wherein a flat portion is formed on the base end side of the needle body.

3. A subcutaneous needle according to claim 1, wherein the separate paper is divided into a side having a central hole and a side without the central hole.

4. A method of producing a subcutaneous needle comprising the steps of:

sticking a separate paper having a hole in the central portion thereof on the adhesive surface of a nearly circular adhesive tape having an adhesive surface on one side thereof and a hole in the central portion thereof in a manner that the separate paper can be separated off;

permitting the top end side of a needle body bent in an L-shape to pass through the holes of said adhesive tape and of said separate paper, and arranging the base end side of said needle body on the side of a nonadhesive surface of said adhesive tape nearly in parallel therewith; and injection-molding a resin material onto the nonadhesive surface of said adhesive tape so as to cover the base end side of said needle body.

* * * * *